(12) United States Patent
Hoffman

(10) Patent No.: US 11,938,080 B2
(45) Date of Patent: Mar. 26, 2024

(54) PERSONAL USE EXTRACORPOREAL LOW FREQUENCY SHOCK WAVE INSTRUMENT AND METHODS OF USING SAME

(71) Applicant: MOON POOL LLC, Chatsworth, CA (US)

(72) Inventor: Jonathan Hoffman, Agoura Hills, CA (US)

(73) Assignee: MOON POOL LLC, Chatsworth, CA (US)

( * ) Notice: Subject to any disclaimer, the term of this patent is extended or adjusted under 35 U.S.C. 154(b) by 0 days.

(21) Appl. No.: 17/693,275

(22) Filed: Mar. 11, 2022

(65) Prior Publication Data

US 2022/0249319 A1 Aug. 11, 2022

Related U.S. Application Data

(63) Continuation of application No. 16/515,244, filed on Jul. 18, 2019, now Pat. No. 10,653,581.

(60) Provisional application No. 62/717,904, filed on Aug. 12, 2018.

(51) Int. Cl.
| | | |
|---|---|---|
| A61H 23/00 | (2006.01) | |
| A61B 17/225 | (2006.01) | |
| A61N 1/00 | (2006.01) | |
| A61N 7/00 | (2006.01) | |

(52) U.S. Cl.
CPC .......... *A61H 23/008* (2013.01); *A61B 17/225* (2013.01); *A61H 2201/0153* (2013.01); *A61H 2201/1207* (2013.01); *A61H 2201/1418* (2013.01); *A61H 2201/1602* (2013.01); *A61H 2201/5058* (2013.01); *A61N 1/00* (2013.01); *A61N 2007/0008* (2013.01)

(58) Field of Classification Search
CPC .................. A61H 23/00; A61H 23/008; A61H 2201/1207; A61H 2201/0153; A61H 2201/1602; A61H 2201/5058; A61H 1/00; A61N 2007/0008
See application file for complete search history.

(56) References Cited

U.S. PATENT DOCUMENTS

| | | | | |
|---|---|---|---|---|
| 5,794,325 A | * | 8/1998 | Fallandy | B25D 11/108 29/566.4 |
| 6,795,950 B2 | * | 9/2004 | Matsushita | H05K 3/0005 700/98 |
| 9,889,066 B2 | * | 2/2018 | Danby | A61H 23/0254 |
| 10,653,581 B2 | * | 5/2020 | Hoffman | A61H 23/008 |
| 11,304,870 B2 | * | 4/2022 | Hoffman | A61H 23/008 |
| 2009/0270915 A1 | * | 10/2009 | Tsai | A61H 1/008 606/238 |
| 2015/0005679 A1 | * | 1/2015 | Becse | A61N 1/0452 607/59 |

(Continued)

*Primary Examiner* — Justine R Yu
*Assistant Examiner* — Matthew R Moon
(74) *Attorney, Agent, or Firm* — SLEMAN & LUND LLP

(57) ABSTRACT

A treatment device includes a housing having a longitudinal axis extending between a proximal end and a distal end, a motor, a drive shaft operatively coupled to the motor, a compression spring at least partially disposed about the drive shaft, a helical cam disposed adjacent the compression spring, the helical cam having at least one discontinuity, a hammer coupled to the helical cam and moveable therewith, and a tip disposed adjacent the distal end.

18 Claims, 13 Drawing Sheets

(56) References Cited

U.S. PATENT DOCUMENTS

2016/0136045 A1* 5/2016 Schlosser ............... A41B 11/00
                                                                  2/243.1
2017/0020778 A1* 1/2017 Bohlinä ............. A61H 23/0254

* cited by examiner

PERSONAL USE EXTRACORPOREAL LOW FREQUENCY SHOCK WAVE INSTRUMENT AND METHODS OF USING SAME

CROSS-REFERENCE TO RELATED APPLICATIONS

The present application is a continuation of U.S. application Ser. No. 16/824,696, filed Mar. 20, 2020, which is a continuation of U.S. application Ser. No. 16/515,244, filed Jul. 18, 2019, now U.S. Pat. No. 10,653,581, and claims priority to U.S. Provisional Patent Application Ser. No. 62/717,904, filed Aug. 17, 2018, entitled "PERSONAL USE EXTRACORPOREAL LOW FREQUENCY SHOCK WAVE INSTRUMENT," the contents of which are hereby incorporated by reference in their entirety as if fully set forth herein.

FIELD OF THE DISCLOSURE

The present disclosure relates to non-invasive home use medical devices. More particularly, the present disclosure relates to non-invasive home use medical devices utilizing low frequency shock waves.

BACKGROUND OF THE DISCLOSURE

Low frequency extracorporeal shock wave treatments have been used in the professional medical community to treat various ailments. For example, the treatment methodology has been demonstrated to be effective in treating soft tissue injuries or damage, reducing fatty deposits commonly known as cellulite, and most recently for the treatment of male erectile dysfunction.

The basic mechanism of treatment is the direct application of the low frequency shock wave generating device on the patient's skin in the desired treatment area wherein the high repetition count of the generated shock waves causes micro-trauma to the underlying tissue. In the case of cellulite, the fat deposits are broken up and reduced in mass and the irregular appearance of the skin's surface is reduced. In the case of soft tissue, the micro-trauma causes the destruction of existing small blood vessels and the subsequent re-growth of a larger number of new blood vessels in the affected area. This enhancement of the circulatory pathways is believed to contribute to the rapid healing of and/or enhanced blood flow to the subject area. Similarly, for the treatment of erectile dysfunction when the cause is related to reduced blood flow in the penis, the micro-trauma induced destruction of local small blood vessels and subsequent regrowth of a greater number and density of small blood vessels increases blood flow to the penis thereby effectively curing erectile dysfunction.

SUMMARY OF THE DISCLOSURE

In some embodiments, a treatment device includes a housing having a longitudinal axis extending between a proximal end and a distal end, a motor, a drive shaft operatively coupled to the motor, a compression spring at least partially disposed about the drive shaft, a helical cam disposed adjacent the compression spring, the helical cam having at least one discontinuity, a hammer coupled to the helical cam and moveable therewith, and a tip disposed adjacent the distal end.

In some embodiments, a treatment device includes a housing having a longitudinal axis extending between a proximal end and a distal end, a first element disposed at the distal end of the housing, a motor, and a second element operatively coupled to and driven by the motor, wherein movement of the second element results in repeated contact with the first element resulting in a shock wave of between 10 and 20 hertz.

BRIEF DESCRIPTION OF THE DRAWINGS

Various embodiments of the presently disclosed treatment devices are disclosed herein with reference to the drawings, wherein.

Figure 1A:
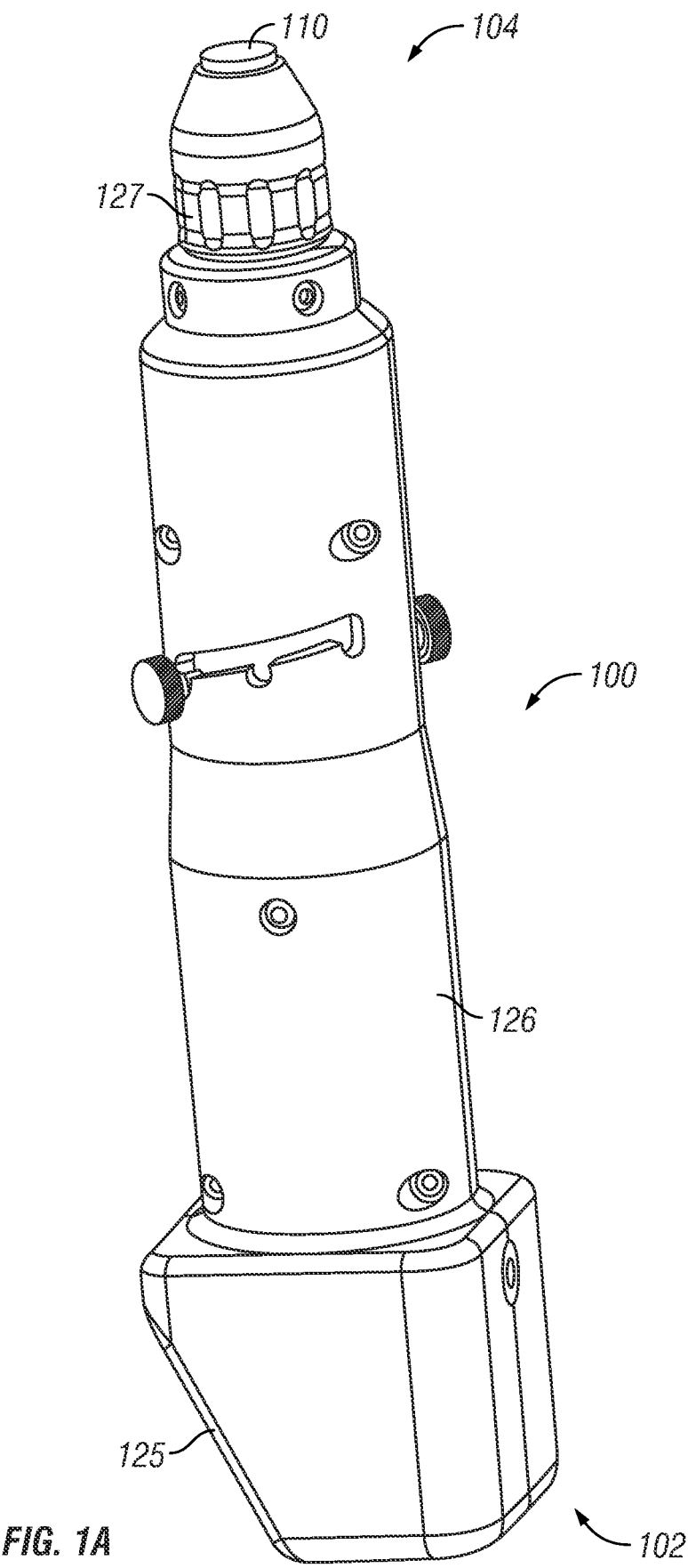
FIG. 1A shows a perspective view of one embodiment of the disclosure.

Various embodiments of the present disclosure will now be described with reference to the appended drawings. It is to be appreciated that these drawings depict only some embodiments of the disclosure and are therefore not to be considered limiting of its scope.

DETAILED DESCRIPTION OF THE DISCLOSURE

Despite the various improvements that have been made to shock wave treatment devices, conventional devices suffer from some shortcomings.

There therefore is a need for further improvements to the devices, systems, and methods of manufacturing and using shock wave treatment devices. Among other advantages, the present disclosure may address one or more of these needs.

As used herein, the term "proximal," when used in connection with a component of a treatment device, refers to the end of the component farthest from the treatment area, whereas the term "distal," when used in connection with a component of a treatment, refers to the end of the component closest to the treatment area.

Likewise, the terms "trailing" and "leading" are to be taken as relative to the operator of the treatment device. "Trailing" is to be understood as relatively closer to the operator, and "leading" is to be understood as relatively farther away from the operator or closer to the target site of treatment.

In conjunction with the included drawings, this detailed description is intended to impart an understanding of the teachings herein and not to define their metes and bounds. One particular implementation, illustrating aspects of the present teaching, is presented in detail below. Some of the many possible variations and versions are also described.

At present, all known commercially available devices utilize one of several technologies to create the low frequency shock waves. These technologies include electrostatic and pneumatic approaches. Such technologies are intrinsically costly, complex, fragile, and bulky. Notwithstanding these disadvantages, existing low frequency shock wave devices have been commercially successful in the professional marketplace because they offer remarkable results in the treatment of several disorders.

The most rudimentary solution to the problem of administering a low frequency shock wave treatment to an area of the body for soft tissue damage, cellulite reduction, or erectile dysfunction treatment is to pay a trained professional to utilize industrial grade, costly equipment to administer the treatment in a professional treatment office setting for a fee.

Another solution to the problem of administering a low frequency shock wave treatment to an area of the body for soft tissue damage, cellulite reduction, or erectile dysfunction treatment is for the individual to purchase an industrial grade treatment device and self-administer treatments.

Yet another solution to the problem of administering a low frequency shock wave treatment to an area of the body for soft tissue damage, cellulite reduction, or erectile dysfunction treatment is for the individual to purchase any of several consumer grade devices which generate low frequency shock waves in order to self-administer treatments.

One area of deficiency generally present in all of these proposed solutions is the high cost of the equipment and or services to administer treatment.

Another area of deficiency generally present in all of these proposed solutions is the time required to make an appointment and attend scheduled appointments in a professional treatment office.

Another area of deficiency generally present in these proposed solutions is the personal embarrassment associated with discussing very personal medical issues with a stranger in order to obtain treatment services.

Yet another area of deficiency generally present in the proposed solutions is the high level of specialized training and medical knowledge necessary to properly operate and administer effective treatments.

Yet another area of deficiency generally present in the proposed solutions is the necessity of a second person to administer treatments to various parts of the body due to the form factor of the applicator which is traditionally in the shape of and held in the fashion of a pistol.

Yet another area of deficiency generally present in the proposed solutions is the substantial size and weight of the system, which generally has a base unit tethered to the applicator device, thereby making transportation, storage, and use difficult and cumbersome.

Still another area of deficiency generally present in the proposed solutions is the absence of any communication connectivity which would facilitate patient tracking or permit updates and upgrades to the operating system of the device.

Still yet another area of deficiency generally present in the proposed solutions is the absence of any automation, or instruction, or artificial intelligence or tutorial capability in any devices presently known.

Still yet another area of deficiency generally present in the proposed solutions is the absence of any communication connectivity which would permit electronic sales, marketing, or promotional materials.

While there are presently a number of proposed solutions to the problem of administering a low frequency shock wave treatment to an area of the body for soft tissue damage, cellulite reduction, or erectile dysfunction treatment none has been conceived or implemented to permit a safe, inexpensive, selfapplied, home use solution which does not require a second person to operate, significant medical or anatomical knowledge, special training, and which provide for tutorials, patient tracking, system updates, and marketed, sales, and promotion capabilities, which permit self-applied low frequency shock wave treatment for various parts of the user's body which would be optimal for the application.

Low frequency shock wave application means embodying the principles of this disclosure solve the problems of a safe, inexpensive, self-applied, home use solution which does not require a second person to operate, significant medical or anatomical knowledge, special training which permits self-applied low frequency shock wave treatment for various parts of the user's body. The several embodiments of the disclosure employ designs, materials, and manufacturing methods which are inexpensive and consistent with current manufacturing practices. The functionality, size, cost, simplicity, ease of use, reliability and robustness of the proposed designs are all advantageous.

Implementations following the principles of this disclosure allow the advantageous modality of safe, inexpensive, self-applied, home use solution which does not require a second person to operate, significant medical or anatomical knowledge, special training which permit self-applied low frequency shock wave treatment for various parts of the user's body which would be optimal for the application.

FIG. 1A shows a perspective view of one embodiment of a treatment device 100 extending between a proximal end 102 and a distal end 104. Device 100 includes a housing 126 in the general form of an elongated cylinder which is easily and conveniently grasped in the user's hand in such a manner as to advantageously permit the user to accurately place tip 110 on the desired area of the body to apply treatment. Tip 110 may be formed of metals, such as steel, aluminum, magnesium, titanium or other metals or alloys thereof, ceramics, and/or a range of plastics and engineering resins including glass-filled nylon, polycarbonates, and other suitable materials. Device 100 further includes a display 125 (e.g., an LCD, LED, or TFT display) disposed on the housing and advantageously positioned so as to permit an unobstructed line of site for the viewer during most normal usage. An end cap 127 is positioned on an opposing end of the housing (i.e., adjacent distal end 104) and is easily accessible and removably attached to housing 126 by any of a variety of conventional means including an internal screw thread, an interrupted thread, a snap lock or any of a variety of mechanical fasteners, so as to facilitate the simple installation, removal, replacement, or switching of tip 110 as required for the selected treatment. A variety of tips may be made of different materials or masses, or different geometries for purposes of advantageously transferring and focusing or diffusing the shock energy depending on the treatment type and desired result. In the preferred embodiment, end cap 127 is secured to housing 126 by an interrupted thread which requires no tools and only a partial rotation to remove and replace.

Figure 1C:
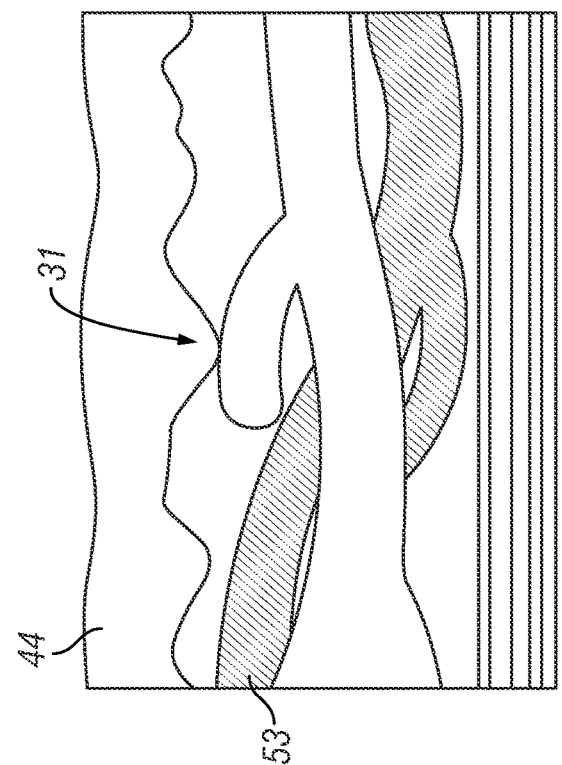
FIG. 1C is a cross sectional view of the human body showing re-regrowth of blood vessels after micro-trauma.
Figure 1B:
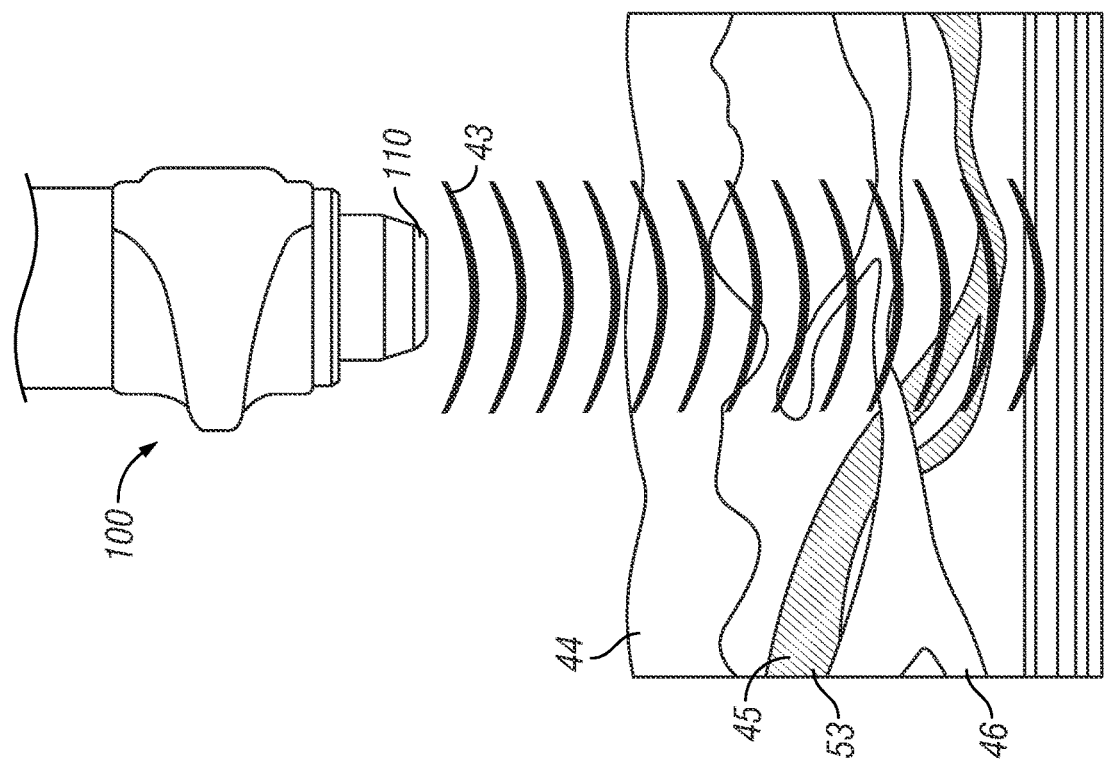
FIG. 1B is a cross sectional view of the human body showing an area targeted for micro-trauma by one embodiment of the disclosure.

Turning now to FIG. 1B, a cross-sectional view of body tissue 44 in targeted treatment area 31 is shown. It may be plainly seen how tip 110 of treatment device 100 when placed in contact with targeted treatment area 31 emits low frequency sonic waves 43 which interact with the smallest blood vessels 53 in the targeted treatment area 31 including veins 45 and arteries 46. The nature of the interaction of sonic waves 43 which are so generated as to be of a frequency of approximately 10 to 20 hertz (e.g., 15 hertz) and of such amplitude as to penetrate body tissue 44 to a depth adequate to reach target blood vessels is to cause damage to the blood vessels 53, commonly referred to as micro-trauma. It should be noted that blood vessels 53 are of a relatively small diameter and low density within body tissue 44.

Referring now to FIG. 1C, a cross-sectional view of body tissue 44 is shown subsequent to treatment with low frequency shock wave device 100. As shown, blood vessels 53 which had been damaged by micro-trauma as a result of the application of sonic waves generated and applied by low frequency shock wave device 100 have now re-grown or healed post-trauma to be both larger in diameter and of a higher density in body tissue 44, thereby facilitating an increased blood flow in targeted treatment area 31.

Figure 2:
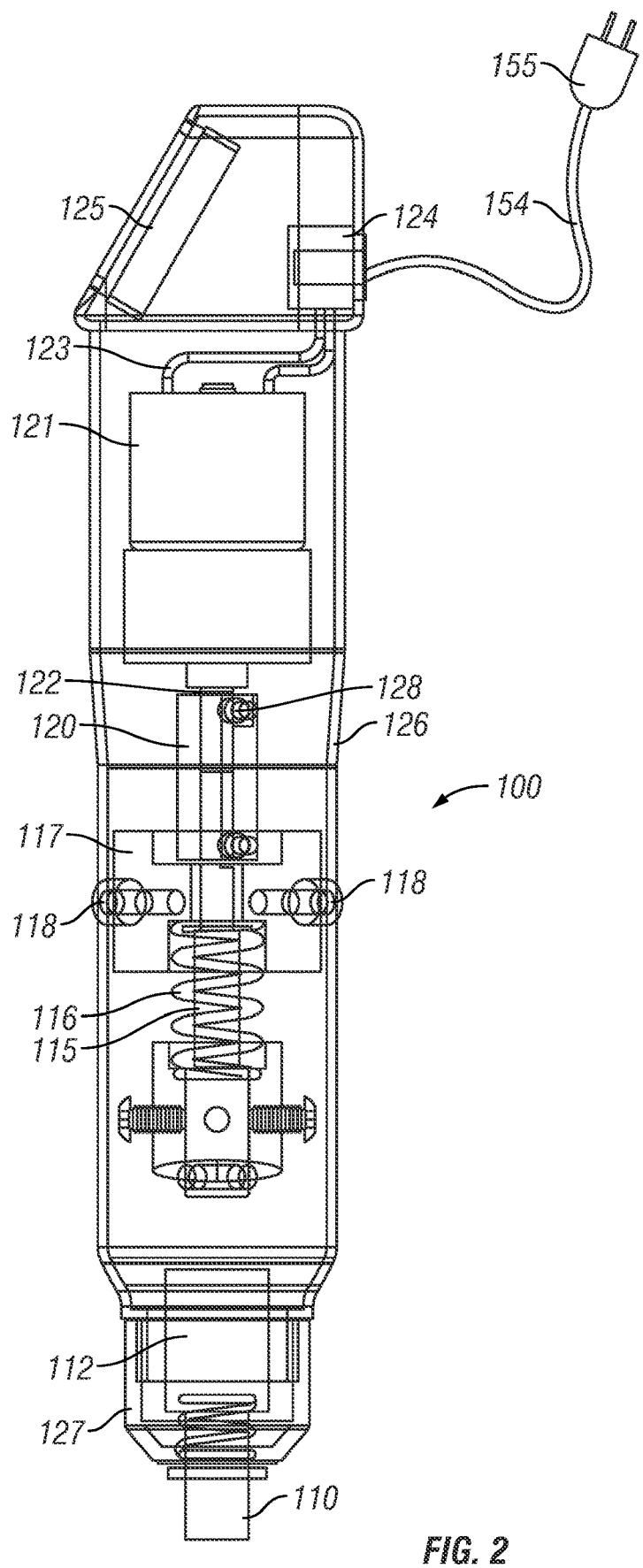
FIG. 2 is a side schematic representation of one embodiment of the disclosure showing major components used to create and administer low frequency shock waves.

Further details of treatment device 100 will now be described with references to FIGS. 2-10B. Referring now to FIG. 2, a schematic view of the assembly of one embodiment of the disclosure is shown, the arrangement of certain major components being visible. In this manner, the operation of the device 100 may be readily understood. Motor 121 is non-rotatably mounted within housing 126 so as to inhibit the rotation of the body of motor 121 but to permit the rotation of motor output shaft 122 when a suitable electrical signal is introduced into motor wiring 123. In one embodiment of the disclosure, motor wiring 123 are connected to power plug receptacle 124 so as to provide a means of attaching and detaching a suitable power supply. In one embodiment a suitable power plug emanating from an electrical transformer which plugs into a wall receptacle, to plug into the device to provide electrical power. In another embodiment of the disclosure, motor wiring 123 are connected directly to an alternating power cord 154 terminated by electrical plug 155 which plugs directly into a wall receptacle. In yet another embodiment, motor wiring 123 are attached to a suitable power plug receptacle 124 which can accept a rechargeable or replaceable battery to cordlessly power the device.

Still referring to FIG. 2, it may be plainly seen that when motor 121 is electrically energized, motor output shaft 122 rotates. The rotation of motor output shaft 122 is translated to drive shaft 115 because motor output shaft 122 and drive shaft 115 are operably coupled (e.g., rigidly connected) to one another by means of shaft coupler 120 which is secured to motor output shaft 122 and drive shaft 115 by means of set screws 128 (or other mechanical or chemical means including adhesives, welding, crimping, swaging, keyway, splines, or the like). By this means of powered rotation, the helical cam component creates the non-linear acceleration of the reciprocating motion of the device.

Figure 3A:
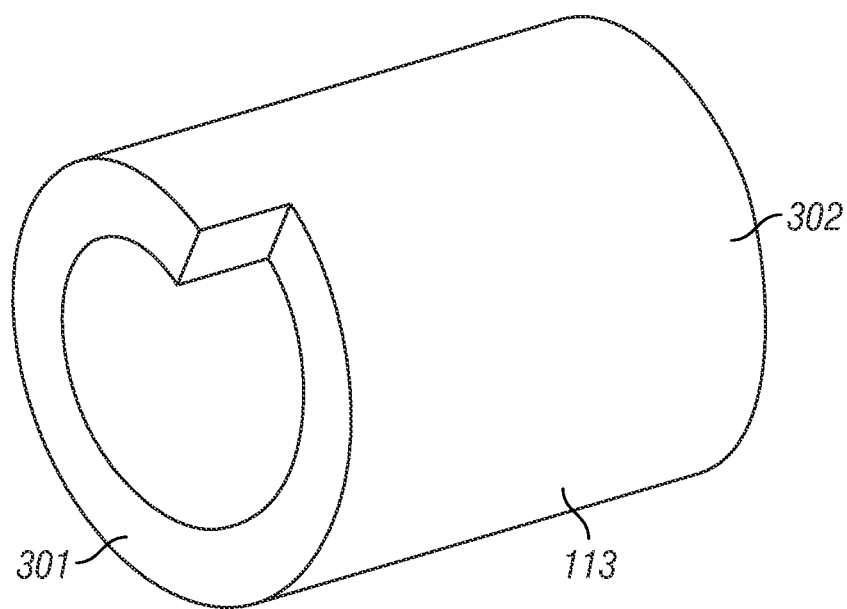
FIG. 3A is a perspective view of a helical cam.

Referring now to FIG. 3A which is perspective view of one embodiment of a helical cam 113, it may be plainly seen that the distinctive ramp and precipitous drop off of the cam profile causes a non-linear reciprocating motion to be imparted to an object following the surface of the cam as the cam rotates. Helical cam is generally formed as a cylinder having two ends, a leading end 302 and a trailing end 302. Trailing end 302 may have a substantially circular cross-section (i.e., the end is flat), while leading end 301 may have a more complex configuration including one or more ramps (e.g., one, two, three or four or more ramps) interrupted by precipitous drops.

Figure 3B:
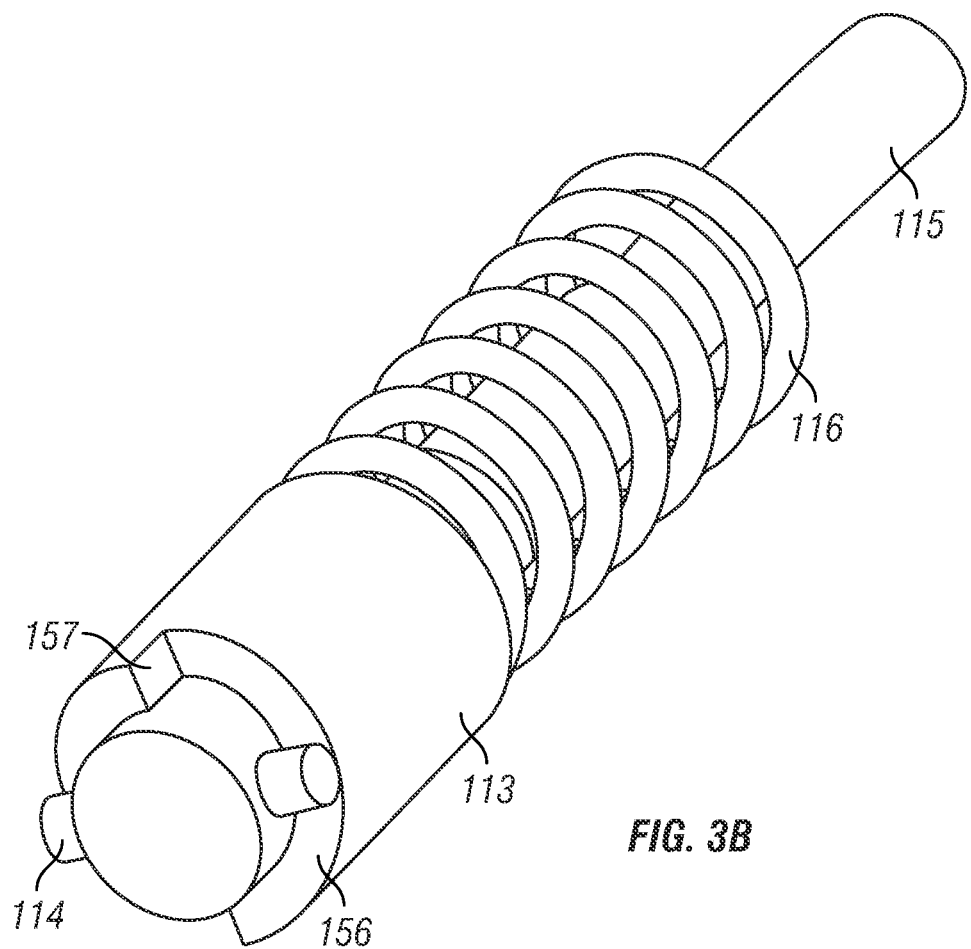
FIG. 3B is a perspective view of one embodiment of a helical cam drive assembly.

Referring now to FIG. 3B, which is a perspective view of a helical cam, drive shaft and cam follower assembly, it may be plainly seen how the mechanism functions. Drive shaft 115 is rigidly affixed to and rotated by motor 121 (not shown in this figure for purposes of clarity). Cam follower 114 is rigidly affixed to drive shaft 115 and rides along the irregular cut helical cam surface 156 of helical cam 113. Compression spring 116, the rearward motion of which is limited by spring base plate 117 (not shown in this figure for purposes of clarity) bears against helical cam 113, imparting a coaxial force against cam follower 114. As cam follower 114 rotates, it rides along helical cam surface 156 and follows its contours. The contours of cam surface 156 are such that each end of cam follower 114 is presented with a steady incline or ramp for approximately half of a revolution or 180 degrees of rotation, and then it drops off precipitously at cam discontinuity 157 back to the lowest initial starting elevation of the ramps. The effect of this helical cam motion is that a constant speed of rotation of drive shaft 115 causes a progressive downward motion of helical cam 113 which in turn causes a continuous compression of compression spring 116 until such time as cam followers 114 drop off the cam discontinuity 157 and helical cam 113 accelerates rapidly upward as a result of the release of energy of compression spring 116.

Device 100 further includes a hammer 112 formed of a metal such as any of the materials described above with reference to the tip 110. In at least some examples, tip 110 and hammer 112 are formed of a same material. Since helical cam 113 is rigidly affixed to hammer 112 (best seen in FIG. 2) and hammer 112 makes contact with tip 110, the rapid, non-linear acceleration of helical cam 113 is translated to hammer 112 which impacts with tip 110 thereby imparting a shock wave to tip 110 which is then communicated to the target treatment area 31 of the user. Without being bound by any particular theory, it is believed that the striking of the hammer on the tip results in shockwave sufficient to cause microtrauma which results in angiogenesis, but that physical contact of the tip with the target area also causes mechanical agitation of the tissue to remove blockages from vessels, which allows blood to flow freely therethrough.

Figure 4:
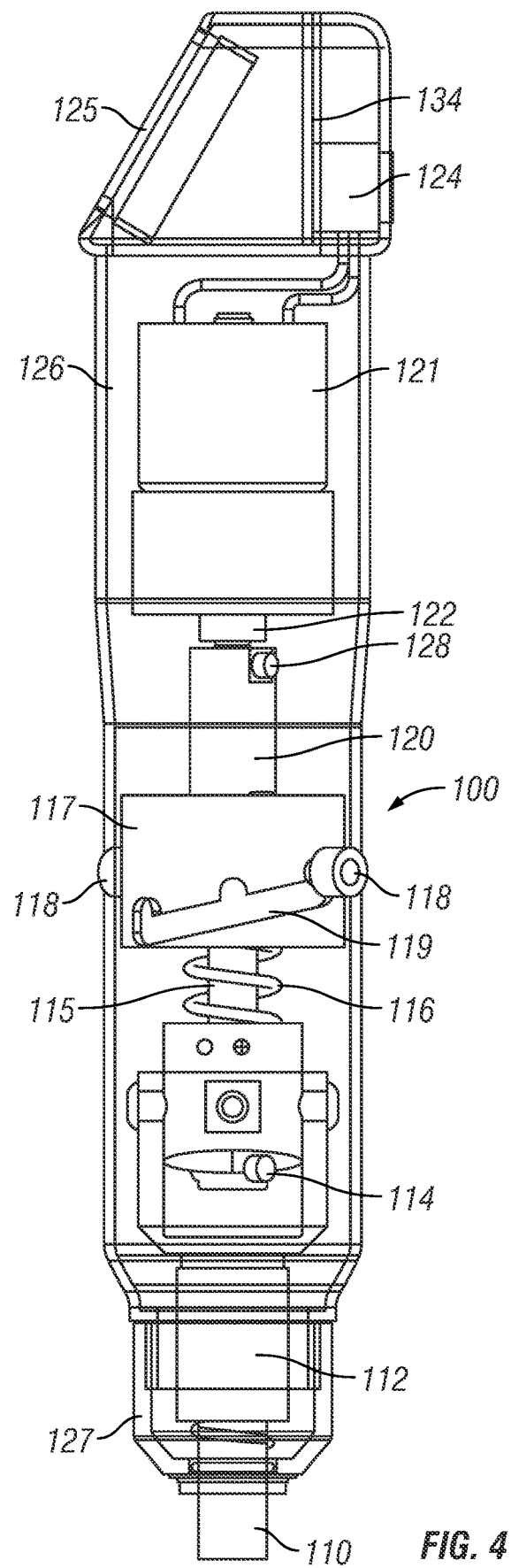
FIG. 4 is a transparent side view of one embodiment of the disclosure.

Referring now to FIG. 4 which is a transparent side view of the device 100, it may be more readily seen how the components and functions described previously are embodied in the device 100. In this view, it may be plainly seen how motor 121 is rigidly affixed by means of motor shaft coupling 120 to drive shaft 115 which terminates with cam followers 114 which follow cam surface 156 of helical cam 113 and compress helical cam 113 against compression spring 116 when motor 121 imparts a rotational force. It may be further seen how helical cam 113 is rigidly affixed to hammer 12 which is so positioned as to impart the rapid acceleration forces to which it is subjected to tip 110 which is secured to device 100 by means of end cap 127, and through which the micro shock forces are imparted to the target treatment area 31 of the user. Still referring to FIG. 4, it may be seen how the initial compressive force or pre-load of compression spring 116 may be adjusted by means of spring base plate 117 being advanced towards tip 110 and thereby compressing compression spring 116 when spring base plate 117 is rotated by means of preload adjust tabs 118 which ride within and follow preload adjust track 119. By this means of rotation, spring base plate 117 is rotatably advanced towards tip 110 so as to decrease the length of the space within which compression spring 116 resides, thereby compressing it and imparting a greater force to helical cam 113 both initially and during the sequence of compression and release which occurs during operation. By this means, the overall force imparted to tip 110 and thereby to targeted treatment area 31 of the user may be adjusted.

As discussed above, drive shaft 115 may be operatively coupled to the motor and may be rotatable. In one variation, drive shaft 115 is not directly affixed to motor 121 but is instead permitted only a reciprocating motion along the longitudinal axis of the device within the elongated housing, while helical cam 113 is operatively coupled (e.g., rigidly affixed) to motor 121 and rotates thereby. In this manner, the same relative motion of drive shaft and helical cam is accomplished to create non-linear reciprocating motion of the drive shaft, but without rotation in the drive shaft. Thus, one of drive shaft and helical cam may perform a first of rotation and translation, and the other the drive shaft and the helical cam may perform the other of the rotation and translation, and in each case the resulting striking of the hammer and the tip is accomplished.

Figure 5:
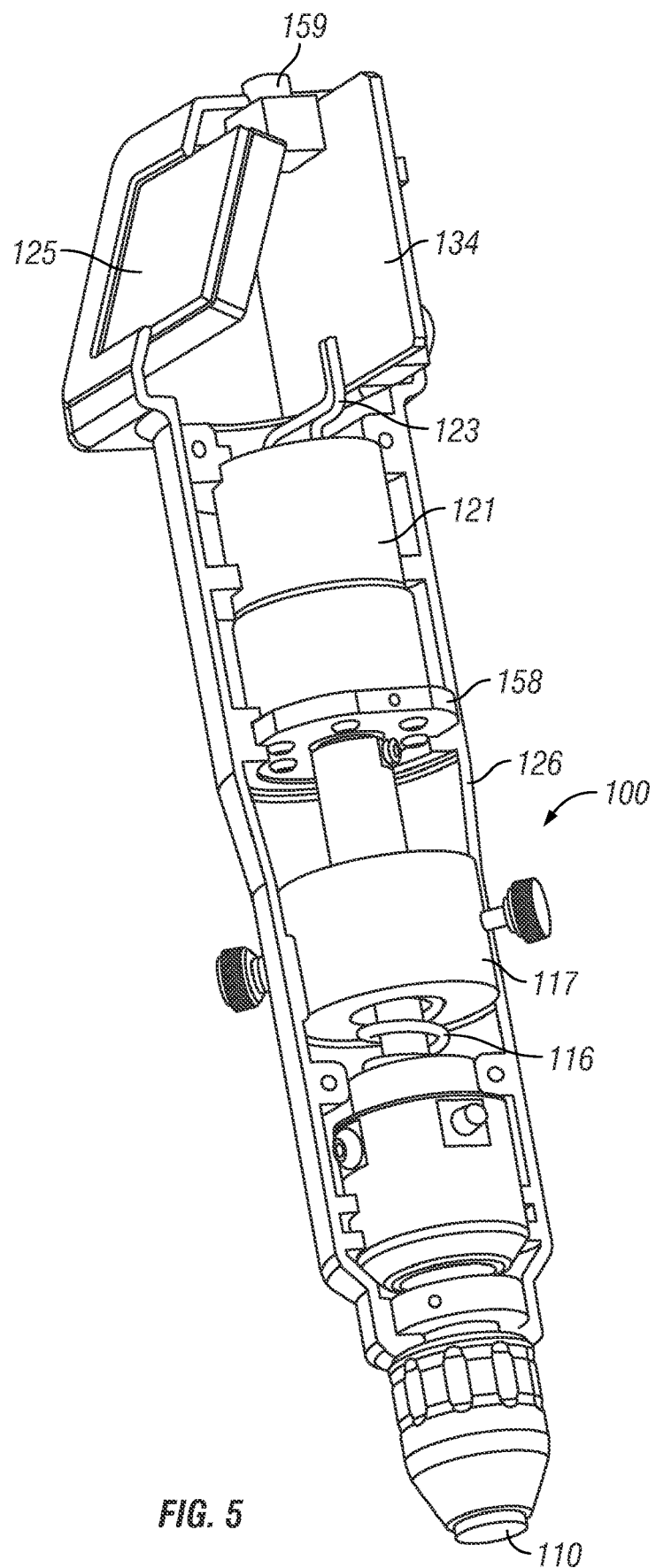
FIG. 5 is a cutaway perspective view of one embodiment of the disclosure.

Referring now to FIG. 5 which is a cutaway perspective view of the preferred embodiment of device 100, several key components may be more plainly seen. In this view, motor mount plate 158 may be seen to provide non-rotatable mounting of motor 121 within housing 126. Also, printed circuit board 134 may be plainly seen. Printed circuit board 134 contains electronic circuitry and controls to produce a stable, reliable power source, to regulate speed of operation, to monitor and display functional parameters such as speed of operation, force, number of cycles, and to accept user inputs such as turning the device on and off or changing speed or force, or resetting counts, as well as generating outputs such as alphanumeric display data or sounds, lights or other enunciators.

Still referring to FIG. 5, it may be plainly seen how display 125 is advantageously incorporated within housing 126 so as to be easily viewable by the user during operation, and power button 159 is similarly conveniently located for easy access and operation by the user.

Figure 6A:
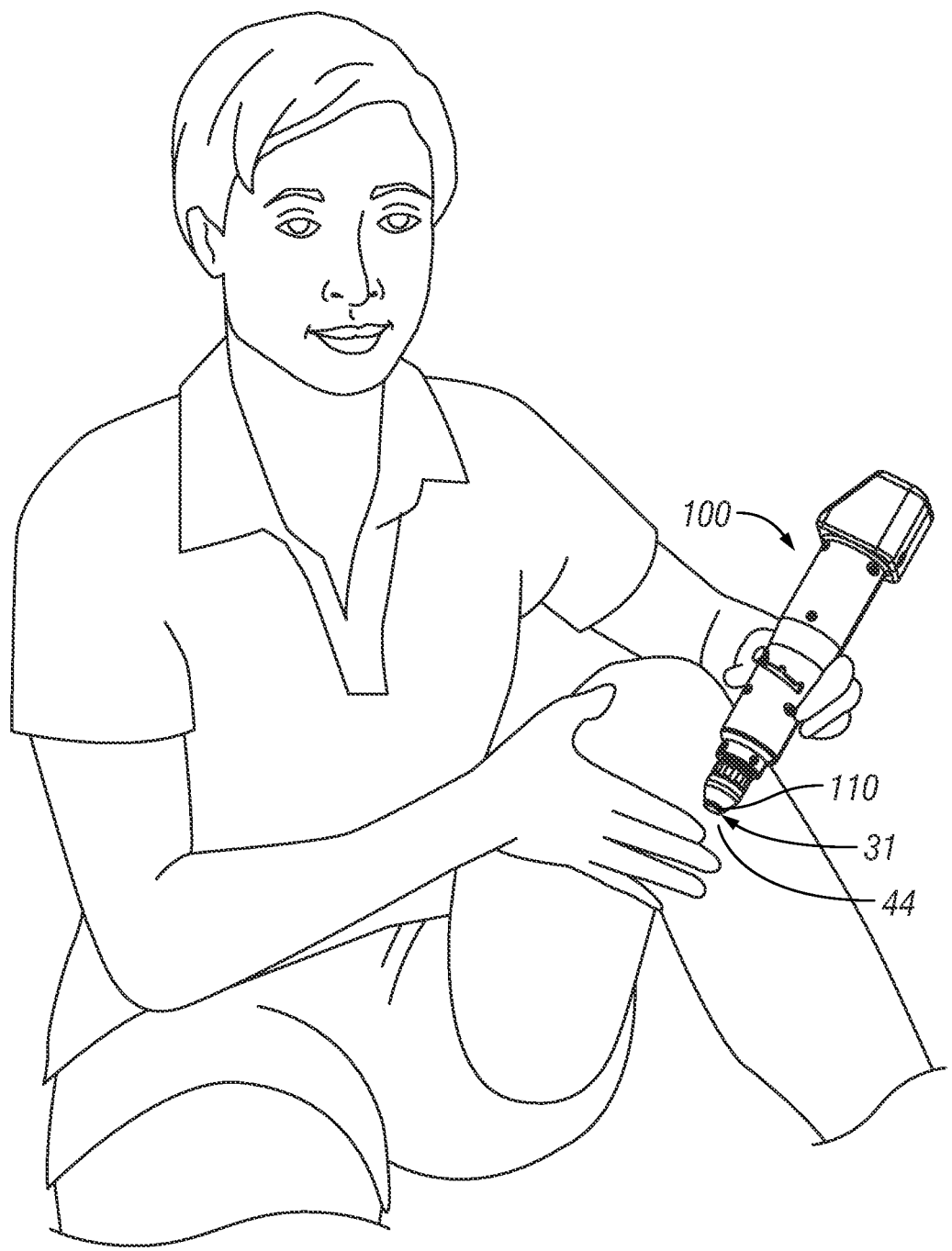
FIG. 6A is a perspective view of one embodiment of the disclosure operated by a user self-administering treatment.

Referring now to FIG. 6A which is a perspective view of the device 100 in operation by a user, it may be plainly seen how the form factor of device 100 is well adapted to be held and deployed by the user to administer self-treatment such that tip 110 may be readily applied to body tissue 44 in target treatment area 31, as opposed to the pistol-like form factor of most commercial devices which are intended for use by a skilled operator for treatments performed on the subject, rather than self-use.

Figure 6B:
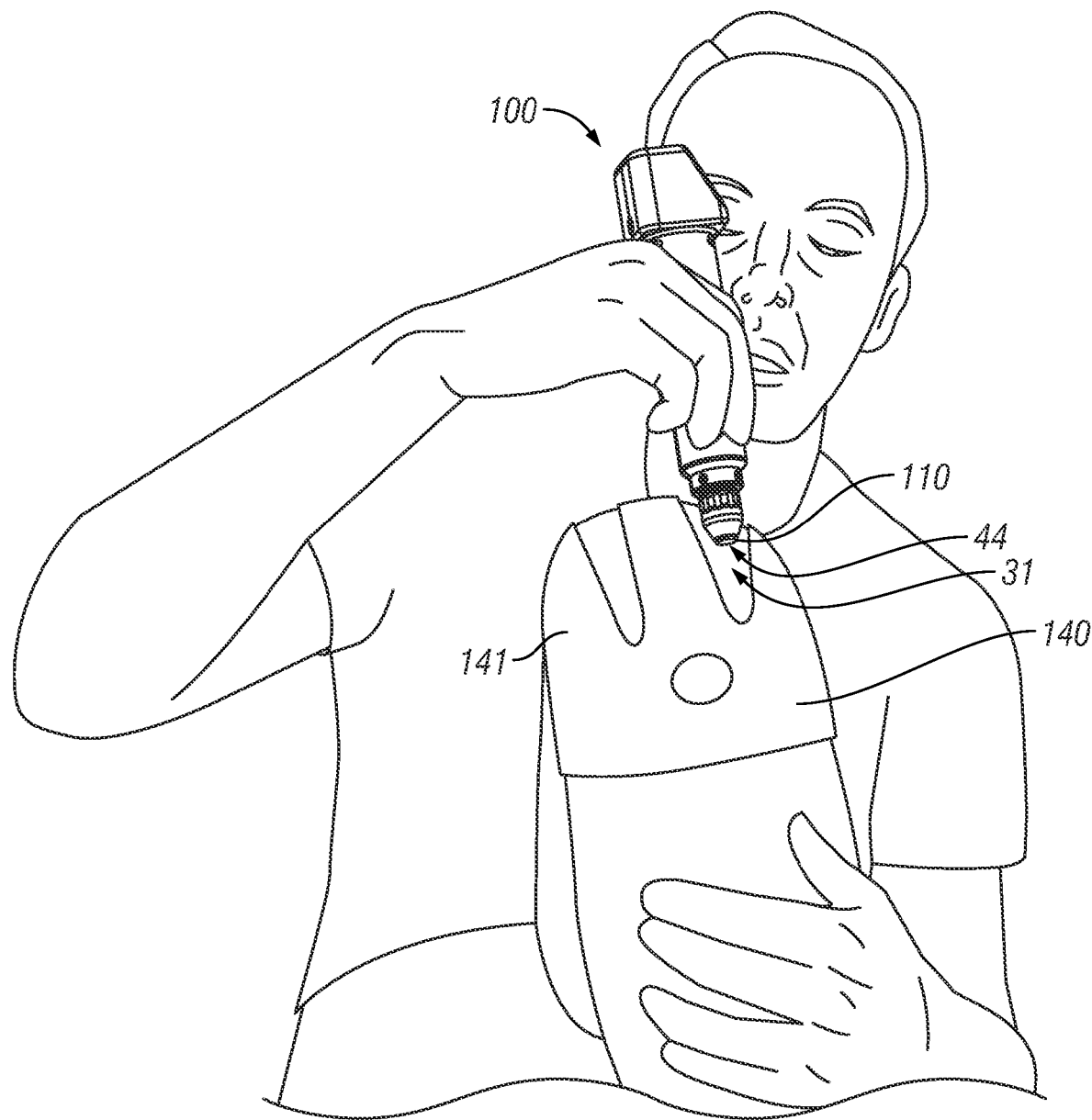
FIG. 6B is a perspective view of one embodiment of the disclosure operated by a user self-administering treatment utilizing a guide template.

Referring now to FIG. 6B, another feature is illustrated. Here it may be plainly seen that the user self administers treatment with tip 110 of device 100 applied to body tissue 44 of target treatment area 31. Given that home use and self-administration of treatments presumes a lack of specialized medical training or anatomical knowledge and given that treatment is most effective when applied properly and correctly to the appropriate target treatment area 31, guide template 140 may be placed over a particular target treatment area 31 such that nontreated areas are obscured and protected by the opaque template material which target treatment areas 31 are exposed by means of guide channels 141 which are openings or windows in guide template 140 such that tip 110 of device 100 may contact body tissue 44 only where accessible through guide channels 141. By this means, even an un-trained user is able to apply treatment to precisely the areas deemed most suitable simply by placing tip 110 of device 100 within guide channels 141 of guide template 140 and moving tip 110 in such a manner as to apply treatment to all areas of exposed body tissue 44 in target treatment area 31.

Figure 7:
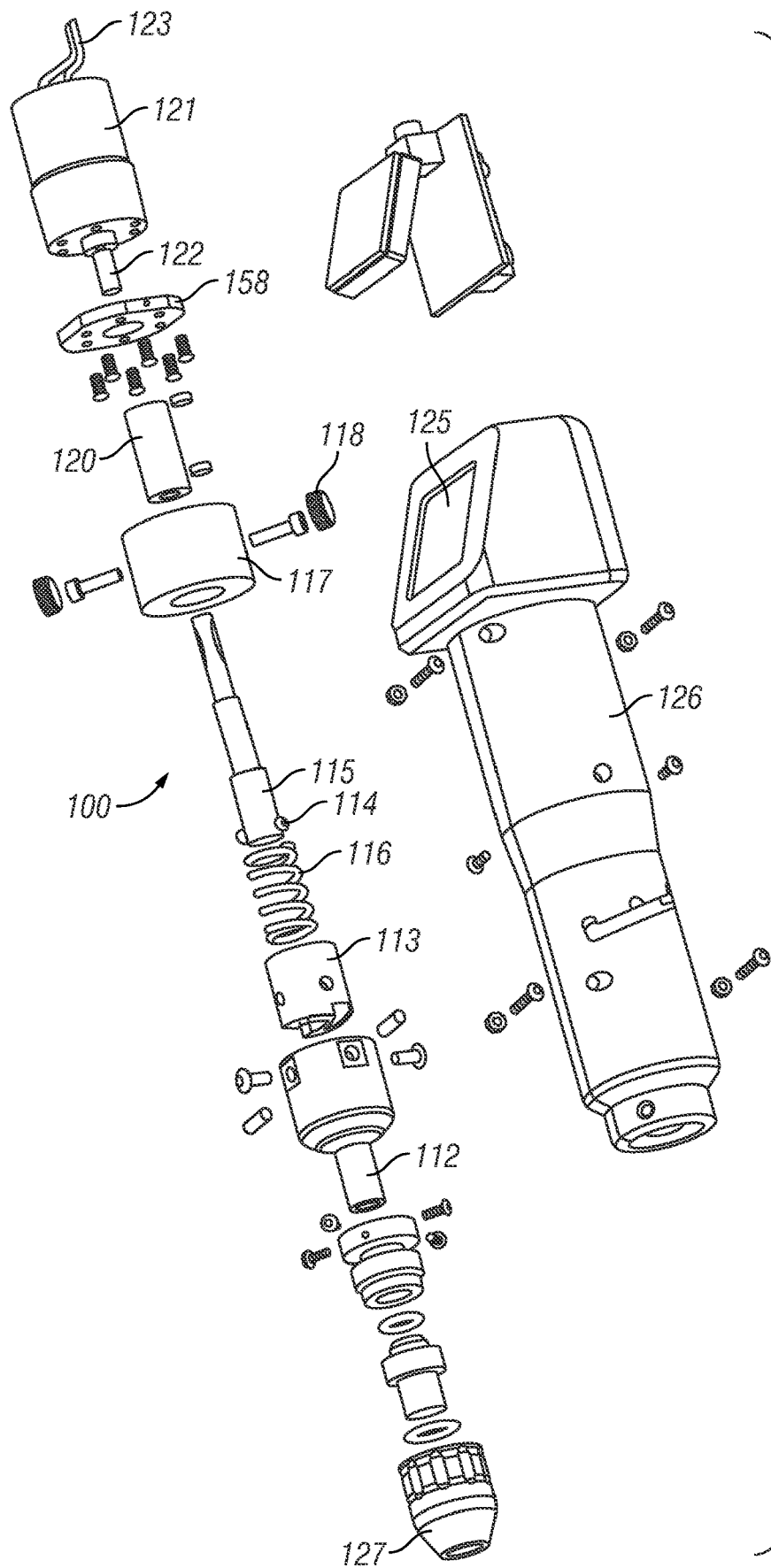
FIG. 7 is an exploded view of one embodiment of the disclosure.

Referring now to FIG. 7 which is an exploded view of the assembly of all components comprising device 100, each of the above referenced items may be clearly seen in its entirety as well as their relative positions within the assembly.

The embodiments disclosed above are merely exemplary and there are many possible variations of the implementations described above consistent with the teaching of the present disclosure which assist the user, particularly a user who does not possess specific medical or anatomical training to utilize the device properly, effectively, safely, and efficiently.

One such variation is the incorporation of a rechargeable or replaceable battery to power the device which enables use without a power cord. This not only affords the user greater mobility and ease of use, not to mention the convenience of being able to use the device outdoors or in a location which does not have electrical receptacles available, but provides the further benefit of increasing the weight of the device, thereby increasing the ratio of the weight of the device relative to the mass of the operating tip which makes it less critical that the user apply pressure to the device against the body to insure that the energy of the tip is being properly transferred to the body.

Figure 8A:
FIG. 8A is a perspective view of one embodiment of the disclosure connected to a smartphone.

FIG. 8A illustrates another variation wherein a smartphone 251 is coupled to device 100 either by a data cable 252 or by some wireless means such as Bluetooth or WiFi, and smartphone 251 is utilized to provide additional or enhanced features or performance for device 100. In one embodiment of the disclosure, smartphone 251 is simply used as a remote display 225 to communicate device status, performance, settings, or other information to the user. There are several advantages to such an arrangement. First, the cost, size, weight, and mechanical vulnerability of a display are removed from device 100. Second, the user may position the smartphone 251 advantageously in order to be able to see the display even when the device is being utilized on a part of the body which does not permit a direct view of display 225 or even device 100 during use. Yet still another feature is the incorporation of plug-in or wireless connectivity of the device to the internet which provides a range of useful features and functions. One such function is the ability to track the individual's usage patterns and history which may be useful in developing and guiding a more effective treatment regimen. Another feature is the ability of the user to access training and use tutorials and instructions through the device or remote monitor. Yet another feature is the ability to monitor, diagnose, troubleshoot or pre-emptively flag service, life cycle, maintenance, updating, or component replacement issues in the device. Still another feature is the ability to update the operating software of the device remotely. Still yet another feature is the ability to present sales and/or marketing information to the user in real time. Yet one more feature is the ability to sell products including refills of expendables such as numbing cream to the user in real time. Yet another feature is the ability to offer additional related or unrelated products and or services for sale to the user in real time. Yet still another feature is the ability for the user to track and monitor progress and results of the treatments over time. Yet one more feature is the ability of the user to access expert assistance or ask and receive answers to questions about the device, use of the device, the treatment protocol, expected results, problems, troubleshooting or other issues by communicating either with a live operator or a database of FAQs.

In another variation device 100 has a video camera built into it to facilitate proper placement of the device when utilized on parts of the body which do not permit a direct line of sight. Video images thus generated may be displayed on a smartphone, computer, TV screen or any of a number of other display devices well known in the art by means of hard wired or wireless connections.

Figure 8B:
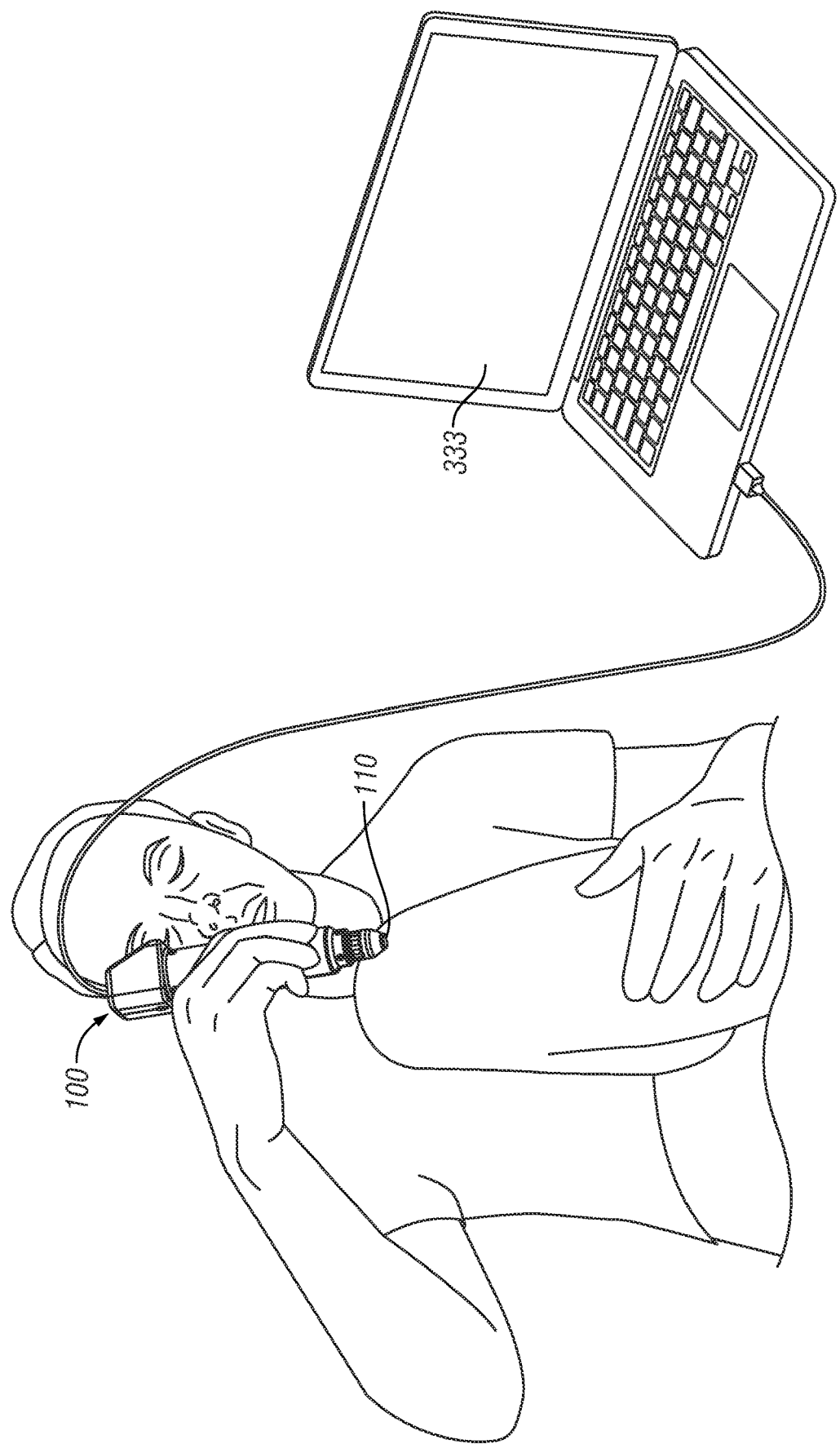
FIG. 8B is a schematic view of one embodiment of the disclosure connected to a computer.

Referring now to FIG. 8B which is a perspective view of one embodiment of the disclosure connected to a computer by means of a data cable it may be plainly seen how all of the capabilities of the device including display, data tracking, data connectivity and sales and marketing opportunities may be employed with a computer 333 coupled to device 100 either wirelessly or by means of a data cable.

Figure 9:
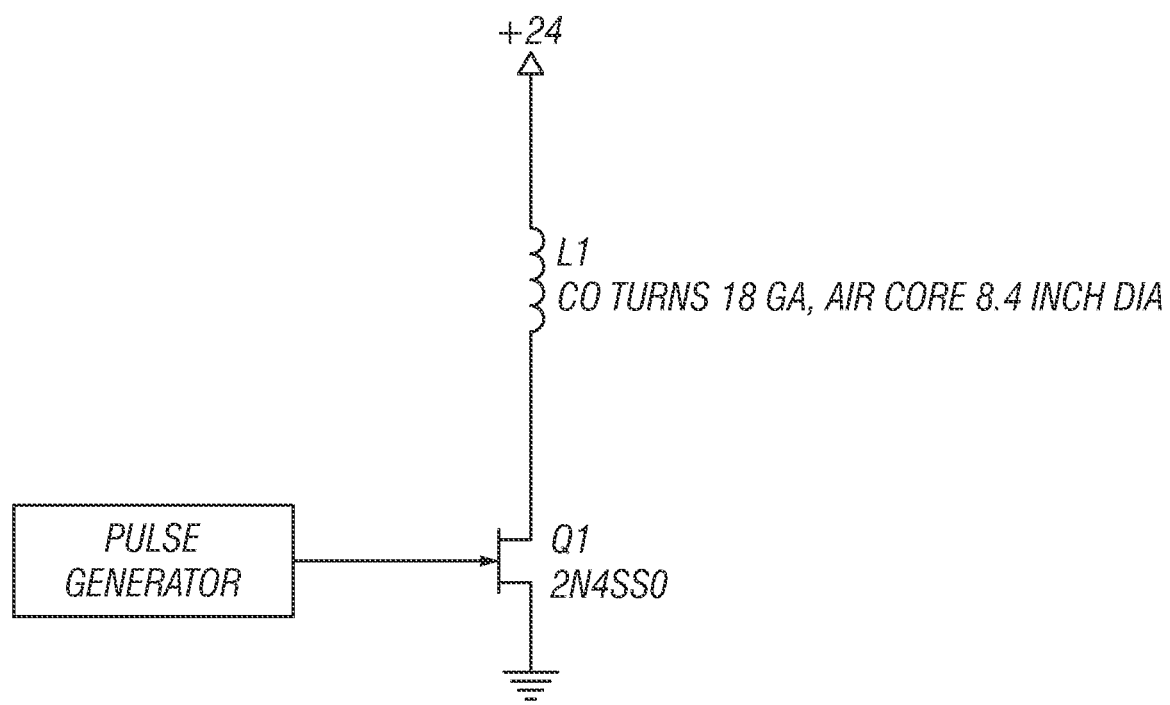
FIG. 9 is an electrical circuit schematic detailing an alternative embodiment of the disclosure.

Referring now to FIG. 9 which is an electrical schematic of a solenoid and driving circuitry, yet another variation of the device may be seen. In this embodiment, the low frequency shock wave energy is created not with a helical cam as in the preferred embodiment, but instead by accelerating a solenoid slug electromechanically by means of a wire coil and colliding said solenoid slug into tip 110 of device 100 to impart the energy to tip 110 which creates the sonic waves 43 required for treatment.

Figure 10A:
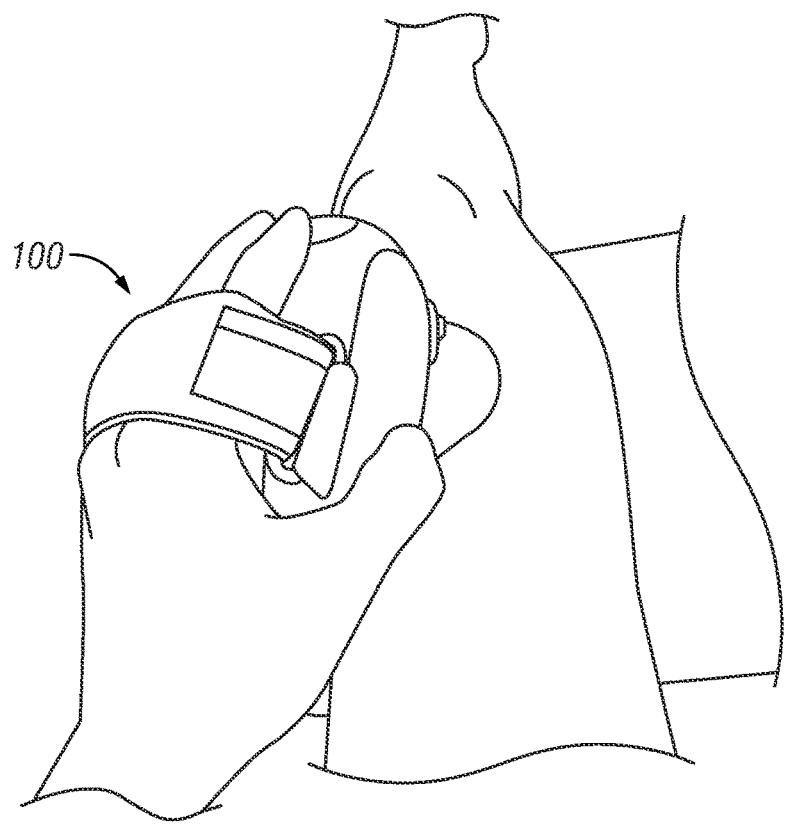
FIG. 10A is a perspective view of an alternate embodiment of the disclosure in use.

FIG. 10A which is a perspective view of another embodiment of the disclosure clearly shows an alternative form factor for the disclosure which facilitates self-treatment, particularly to hard to reach areas of the user's body. In this embodiment the body of device 100 is advantageously cradled in the user's palm while a strap which passes over the back of the user's hand secures the device to the user's hand thereby alleviating the burden of securely grasping the device which may be difficult to accomplish when applying the device to certain hard to reach areas of the body.

Figure 10B:
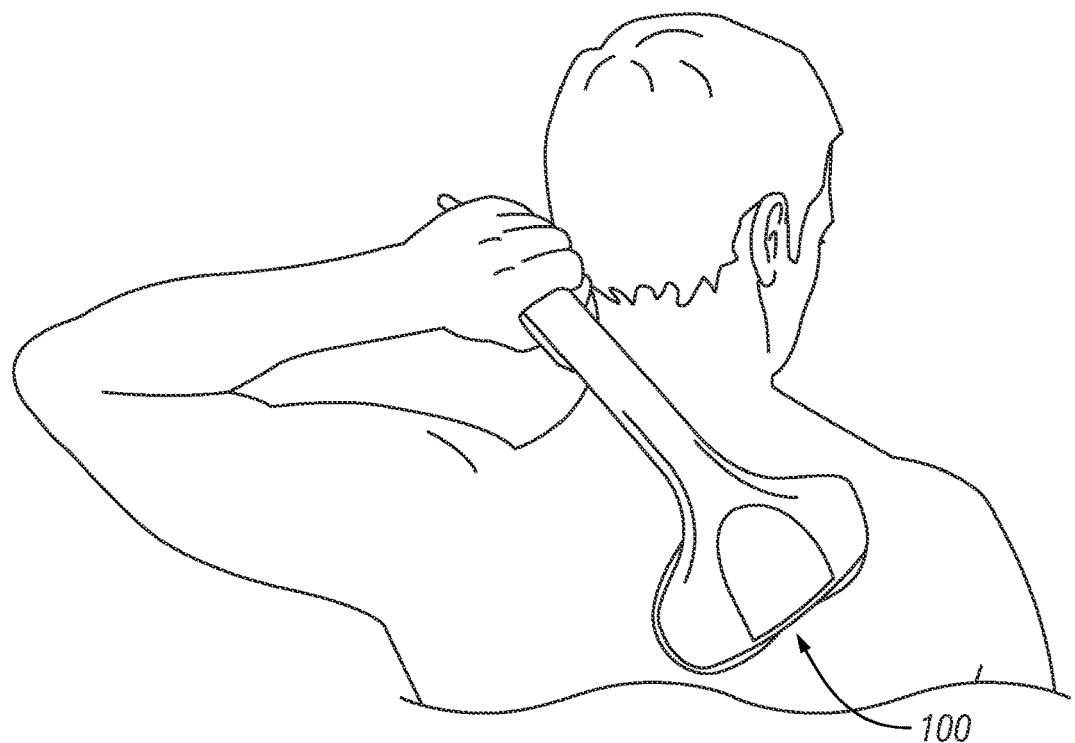
FIG. 10B is a perspective view of yet another alternate embodiment of the disclosure in use.

FIG. 10B which is a perspective view of yet another embodiment of the disclosure clearly shows yet another form factor for the disclosure which facilitates self-treatment, particularly to hard to reach areas of the user's body which may be inaccessible to the user's hand without additional mechanical assistance or extension. In this embodiment which utilizes a handle to functionally extend the reach and range of the user's hand it advantageously permits the user to place tip 10 of the device 100 on areas of the body which might otherwise be out of reach. One further variation of the disclosure is to incorporate a video camera in such an embodiment with the image produced by said video camera viewable on a remote display to advantageously permit the user to locate and place device 100 accurately on parts of the body which are not in direct line of site for example the buttocks or back of thighs, which might be highly desirable treatment locations.

Yet another feature is the incorporation of telemetry in the device which apart from or in cooperation with a constellation of sensors may be used to assist the user in properly locating the device on the desired body part and insuring proper travel, range of motion, and full coverage of the area whether the body part is directly viewable by the user or not.

It may be seen in these several embodiments of the disclosure that the disclosure overcomes the deficiencies of all previous attempts at solving the problem of device which administers low frequency shock waves to targeted areas of the user's body for treatment of soft tissue damage, cellulite reduction, or erectile dysfunction which is a safe, inexpensive, self-applied, home use solution which does not require a second person to operate, significant medical or anatomical knowledge, special training, and which provide for tutorials, patient tracking, system updates, and marketed, sales, and promotion capabilities, which would be optimal for the application.

In broad embodiment, the present disclosure is a device which administers low frequency shock waves to targeted areas of the user's body for treatment of soft tissue damage, cellulite reduction, or erectile dysfunction which is a safe, inexpensive, self-applied, home use solution which does not require a second person to operate, significant medical or anatomical knowledge, special training, and which provide for tutorials, patient tracking, system updates, and marketing, sales, and promotion capabilities, which would be optimal for the application.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:
1. A treatment device comprising:
   a housing;
   a motor disposed within the housing;
   a drive shaft driven by the motor and configured to translate along a first axis;
   a compression spring concentric with the drive shaft;
   a helical cam disposed adjacent the compression spring, the helical cam having a flat end, and an irregular end having at least one discontinuity, the drive shaft passing through the helical cam from the flat end to the irregular end, the helical cam being configured for rotational movement, but being prohibited from translation along the first axis;
   at least one cam follower directly coupled to, and in contact with, the drive shaft and configured to travel along the helical cam, the at least one cam follower being configured to translate along the first axis; and
   a blunt tip aligned with the helical cam, the blunt tip being configured and arranged to contact body tissue to induce a micro-trauma.
2. The treatment device of claim 1, wherein the drive shaft is rotatable.
3. The treatment device of claim 1, wherein the drive shaft is translatable.
4. The treatment device of claim 1, wherein the helical cam is substantially cylindrical and includes at least one gradually inclined ramp along its irregular end, the at least one cam follower being configured to travel along the at least one gradually inclined ramp.

5. The treatment device of claim 4, wherein the at least one gradually inclined ramp includes an incline that extends about the circumference of the helical cam for approximately half of a revolution.

6. The treatment device of claim 5, further comprising a precipitous drop-off after the at least one gradually inclined ramp.

7. The treatment device of claim 6, wherein the at least one gradually inclined ramp includes two gradually inclined ramps.

8. The treatment device of claim 1, further comprising a battery.

9. A system comprising:
   the treatment device of claim 1; and
   a guide template for partially covering a body part and having at least one window through which a treatment area is exposed.

10. A treatment device comprising:
    a housing;
    a motor disposed within the housing;
    a drive shaft driven by the motor and configured to translate along a first axis;
    a compression spring concentric with the drive shaft;
    a helical cam disposed adjacent the compression spring, the helical cam having a flat end, and an irregular end having at least one discontinuity, the helical cam being configured for rotational movement, but being prohibited from translation along the first axis;
    at least one cam follower directly coupled to the drive shaft and configured to travel along the helical cam, the at least one cam follower being configured to translate along the first axis;
    a first element disposed at one end of the housing, the first element including a blunt tip aligned with the helical cam, the blunt tip being configured and arranged to contact body tissue to induce a micro-trauma; and
    wherein movement of the drive shaft causes translation of the first element.

11. The treatment device of claim 10, wherein the helical cam is substantially cylindrical and the irregular end includes at least one gradually inclined ramp.

12. The treatment device of claim 11, wherein the at least one gradually inclined ramp includes an incline that extends about the circumference of the helical cam for approximately half of a revolution.

13. The treatment device of claim 12, further comprising at least one precipitous drop-off formed as a vertical wall aligned with a longitudinal axis of the helical cam, the vertical wall being disposed after the at least one gradually inclined ramp.

14. The treatment device of claim 13, wherein the at least one gradually inclined ramp includes two gradually inclined ramps and two drop-offs.

15. The treatment device of claim 10, further comprising a display disposed on the housing on an opposite end of the first element, the display being capable of providing instructions to a user during use of the treatment device.

16. The treatment device of claim 15, further comprising means for communicating with a smartphone or computer to relay at least one of patient data, device training, guidance and sales information to the display.

17. The treatment device of claim 10, wherein the compression spring is at least partially disposed about the drive shaft.

18. The treatment device of claim 10, wherein the compression spring is fully disposed about the drive shaft.

* * * * *